United States Patent [19]
Carmello et al.

[11] Patent Number: 5,841,009
[45] Date of Patent: Nov. 24, 1998

[54] OXYCHLORINATION OF ETHYLENE IN TWO STAGE FIXED-BED REACTOR

[75] Inventors: Diego Carmello, Veneto; Pierluigi Fatutto, Mestre; Andrea Marsella, Paese, all of Italy

[73] Assignee: EVC Technology AG, Zug, Switzerland

[21] Appl. No.: 894,288

[22] PCT Filed: Feb. 1, 1996

[86] PCT No.: PCT/IB96/00159

§ 371 Date: Oct. 22, 1997

§ 102(e) Date: Oct. 22, 1997

[87] PCT Pub. No.: WO96/26171

PCT Pub. Date: Aug. 29, 1996

[30] Foreign Application Priority Data

Feb. 22, 1995 [GB] United Kingdom .................... 9503541
Apr. 11, 1995 [GB] United Kingdom .................... 9507480

[51] Int. Cl.⁶ ..................................................... C07C 17/15
[52] U.S. Cl. .................................................................. 570/245
[58] Field of Search ................................................ 570/245

[56] References Cited

FOREIGN PATENT DOCUMENTS 0 146 925  3/1985  European Pat. Off. .

*Primary Examiner*—Alan Siegel
*Attorney, Agent, or Firm*—Woodcock Washburn Kurtz Mackiewicz & Norris LLP

[57] ABSTRACT

In the oxychlorination of ethylene to produce 1,2-dichloroethane (EDC), in which ethylene, a chlorine source and an oxygen source are reacted in a fixed-bed oxychlorination reactor in the presence of a catalyst, a twin reactor system is used and the catalyst is a cupric chloride catalyst whose activity profile is arranged such that the reagent flow first comes into contact with a first layer of high activity catalyst, than a second layer of low activity catalyst and finally a third layer of high activity catalyst.

9 Claims, 1 Drawing Sheet

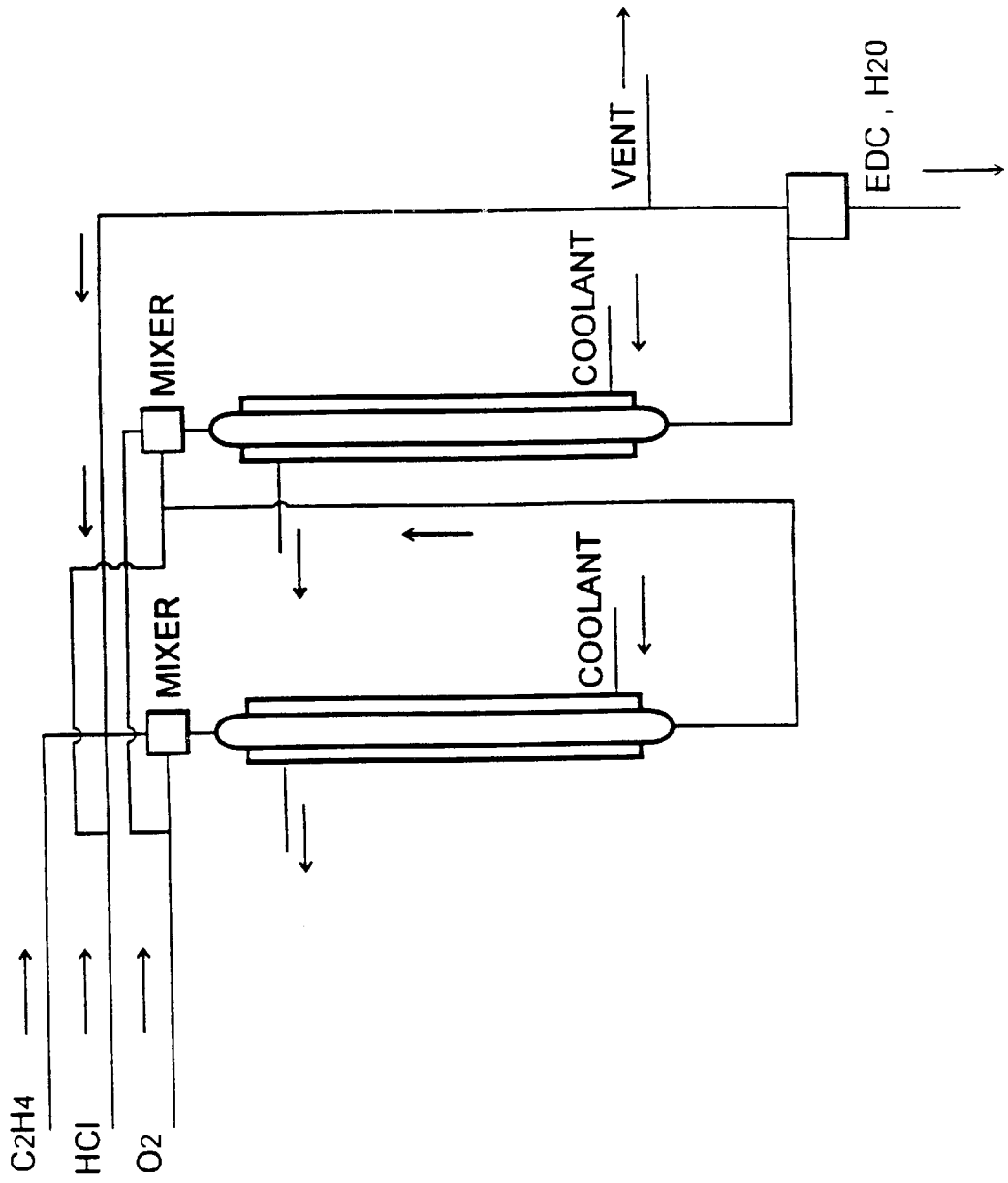

OXYCHLORINATION OF ETHYLENE IN TWO STAGE FIXED-BED REACTOR

This application is a 371 of PCT/IB96/00159 filed Feb. 1, 1995.

The present invention relates to the oxychlorination of ethylene in a fixed bed reactor system which consists of a single reactor, to produce chlorinated hydrocarbons, particularly 1,2-dichloroethane (EDC).

It is well known that hydrocarbons such as ethylene may be chlorinated by reacting them with hydrogen chloride and gases containing elemental oxygen, particularly air or oxygen enriched air, in the presence of a catalyst at elevated temperatures and pressures in order to produce chlorinated hydrocarbons such as EDC. The reaction may be carried out with two different reactor technologies. The first is fluid bed reactor technology wherein a gaseous mixture of reactants is contacted with a fluidizable catalyst powder. The second is fixed bed reactor technology, in which the gaseous reactants flow over a fixed catalyst inside the reactor.

Fluid bed reactors have a number of drawbacks, such as potential stickiness of the catalyst powder, unsteady operation, poor selectivity owing to the gas and catalyst solids back mixing in the reactor, loss of heat transfer owing to fouling of the cooler bundle and limits in reagent velocity imposed by the need to avoid catalyst loss by elutriation from the reactor.

Fixed bed reactor technology has been developed in order to overcome these problems (see U.S. Pat. No. 3,892,816 and U.S. Pat. No. 4,123,467).

Although the fixed bed reactor overcomes many of the problems incurred with the fluid bed reactor system, a number of new problems have been encountered. A major problem is the difficulty, in the fixed bed reactor, of transferring the heat developed by the exothermic oxychlorination reaction away from the reactor to prevent overheating. For this reason, all the necessary reagents may not be fed in the correct stoichiometric ratio to the reactor. Moreover, because it can be unsafe to have an oxygen concentration of above 8% in the mixture feeding the reactor, for flammability reasons, the reaction is carried out in two or more subsequent stages (usually three) such that the ethylene is introduced into the first reactor while the HCl and oxygen feeds are split between the reactors. Unreacted ethylene plus some inert gases are recycled back to the first reactor.

In a further attempt to reduce the incidence of hot spots and the like, it is known to alter the activity profile of the catalyst within a fixed bed reactor such that the activity increases in the direction of flow. For example, see European patent application 0146925. However, in the prior art, even when a profiled catalyst is used it has been deemed necessary to use a multi-reactor system.

The three-reactor systems of the prior art have a number of disadvantages. For example, because the contact time decreases from the first to the third stage, the partial pressure of the reagents is also decreased. This means that the three reactors have to be operated at different temperatures, requiring separate cooling jackets. Moreover, in spite of these precautions, the productivity of each reactor is different. This is particularly notable in the third reactor, where productivity is about 50% of that in the first reactor.

Furthermore, as a result of the high pressure drop which occurs across the whole catalytic bed system in three reactors, the recycling of vent gases necessitates an elevated energy consumption.

Moreover, it is self-evident that setting up and maintaining a three reactor system is more costly that a system involving a single or twin reactors.

We have now developed a new process for the catalytic oxychlorination of ethylene which makes use of a twin reactor system. Owing to a particular catalytic loading scheme, the same EDC productivity as a three reactor system can be maintained, which means that total productivity, with respect to the volume of catalysis involved, is 50% greater than that achievable in a three reactor system.

According to a first aspect of the invention, we provide a method for the oxychlorination of ethylene to produce 1,2-dichloroethane (EDC), comprising reacting ethylene, a chlorine source and an oxygen source in a fixed-bed oxychlorination reactor in the presence of a catalyst, characterised in that a twin reactor system is used and the catalyst is a cupric chloride catalyst whose activity profile is arranged such that the reagent flow first comes into contact with a first layer of high activity catalyst, subsequently a second layer of low activity catalyst and finally a third layer of high activity catalyst.

Preferably, the third layer of catalyst is a profiled catalyst and comprises multiple catalyst layers arranged in order of increasing activity.

Preferably, the catalyst loading pattern according to the invention is applied to both reactors in the two reactor system.

The catalyst loading pattern according to the invention allows the reaction to start quickly as the reagents come into contact with the first, highly active catalyst layer. Before the temperature of the reacting reagents exceeds 270° to 285° C., the reagents flow into contact with the lower activity catalyst layer, thus decreasing the rate and therefore the temperature of the reaction. Advantageously, therefore, the first, highly active catalyst layer is short. In any case, the ideal length of the catalyst layer may be determined empirically, by determining the maximum length of catalyst layer which may be used without the reaction exceeding 285° C.

The second, lower activity catalyst layer is arranged such that the reaction, which has been initiated at a high rate by the first catalyst layer, is not allowed to exceed a hotspot temperature of 285° C.

The third, high activity catalyst layer is arranged such that the maximum conversion of reagents is achieved, without exceeding 285° C. Advantageously, the third catalyst layer is a profiled catalyst layer wherein the activity increases in the direction of reagent flow.

The choice of suitable specific catalyst loading patterns will depend on the maximum forecast temperature of the hotspot, and on the inside diameter and length of the reactor being used, as well as the throughput of reagents.

Catalysts of varying known activities for use in the method of the invention are known in the art. Preferably, the catalysts are supported catalysts with cupric chloride as the active component and alumina, silica gel or aluminosilicates as supports. The support material may be in the form of the spheres, cubes, cones, hollow cylinders, cylindrical pellets, multilobate pellets and the like.

The copper content of the catalyst preferably varies in accordance with the required activity, such that the first, active catalyst layer has a high copper content, the second, lower activity catalyst layer has a lower copper content, and the third, high activity layer has a high copper content. Where the third catalyst is a profiled catalyst, the copper content of the catalyst may be similarly profiled.

In addition to the cupric chloride active component, the catalyst may also comprise promoters such as the chlorides of potassium, magnesium, cesium, lithium, sodium, calcium and cerium for improving the selectivity to EDC.

The reactor type employed in the method of the invention is a tubular reactor. Advantageously, it consists of a plurality of tubes stacked together within a single coolant jacket. The internal diameter of each tube is preferably between 15 and 40 millimeters. Diameters of less than 15 millimeters are disadvantageous as an excessive number of tubes is required in an industrial reactor in order to obtain a satisfactory throughput of materials, while diameters larger than 40 millimeters result in excessively high hotspot temperatures inside the catalytic bed, requiring a low specific throughput in order to keep the temperatures low. A diameter of 20 to 30mm is preferred.

The preferred length of the reactor is between 3 and 9 meters. A length of less than 3 meters results in too short a residence time and therefore either low reactant conversion or low specific throughput; a length of more than 9 meters is not necessary in order to achieve both high HCl and oxygen conversion and large specific throughput. A length of 3.5–7 m is preferred.

Preferably, all of the ethylene is fed into the first reactor, together with from 40 to 100% of the chlorine source. Preferably, the chlorine source is a HCl.

The oxygen source is preferably pure oxygen and the volume of pure oxygen fed to the first reactor is preferably between 2 and 6% by volume of the total fed product in the first reactor, corresponding to between 40 and 60% of the total oxygen fed to the reaction.

In the second reactor, as a different reagent mixture is used which has higher flammability limits, the oxygen concentration may be increased to between 7 and 10% without hazard. The oxygen excess with respect to the stoichiometric requirement in relation to the chlorine source will range from 0 to 15%.

Preferably, unreacted gasses are recycled from the second reactor back to the first reactor. The composition of the recycled gas, which may include some or all of the unreacted ethylene recovered after standard cooling and condensation procedures, will reach an equilibrium depending on combustion rate, amounts of inert gases in the raw materials and the purge rate. Ethylene concentration can accordingly vary from 10% to nearly 90%. As a consequence, the excess of ethylene in the reaction depends on the ethylene concentration in the recycle vent gas and on the recycle flow rate.

Where at least some of the vented ethylene, or other gases, are not recycled, they may be used in other processes, such as direct chlorination.

The recycle flow rate may be adjusted in order to control oxygen concentration at the inlet of the first reactor, thus controlling the hotspot temperature.

The hotspot temperature itself depends on several parameters. Typically, hotspot temperatures of between 230° and 260° C. are preferred for a tubular reactor with an inside diameter of 27 millimeters, and 250° to 275° C. for a tubular reactor with an inside diameter of 32 millimeters.

Preferably, reactants are preheated up to between 100°–200° C. The pressure of the reaction can range up to 20 barg, the preferred pressure in being between 4 and 7 barg.

The performance of the two stage process is excellent. HCl conversion is typically above 98% even with very low oxygen excess and conversion beyond 99% can easily be achieved with an oxygen excess of 10% in the second stage. The selectivity of the reaction, moreover, is high. The burning rate is low, less than 1% of the ethylene being converted to carbon monoxide and carbon dioxide. Byproducts such as ethyl chloride amount to approximately 1500 to 3000 ppm in the EDC produced.

The invention will now be described, for the purpose of illustration only, in the following examples. FIG. 1 shows a schematic diagram of a two reactor system according to the invention.

COMPARATIVE EXAMPLE 1

The reactors were three units composed of 313mm (1.25 inch) o.d. nickel tube, 14 BWG, 14 feet long; inside each tube, on axis, there was a thermowell of 6mm o.d. containing 4 sliding thermocouples with which it was possible to record the thermal profile of the reactor. The reactor was surrounded with an external jacket in which steam at 210° C. and 18 barg was used to control the temperature of the reaction. The reactor pressure was controlled with a pneumatic valve on an effluent line.

The reagents were preheated in 18 barg steam heated exchangers. Ethylene, HCl and nitrogen were mixed together and oxygen was added to the mixture in a special mixer where the velocity of the gases was higher than the eventual ethylene flame propagation velocity. The catalyst used was a normal industrial catalyst for a three stage fixed bed process consisting of hollow cylinders containing copper and potassium chloride arranged as follows:

In the first reactor, 60% of the volume was gilled with a catalytic bed containing Cu 3.2% w/w, K 1.3% w/w and Cs 1.4% w/w. The other 40% was filled with a catalytic bed containing Cu 5.5% w/w, K 1.8% w/w and Cs 2.0% w/w. In the second reactor 60% of the volume was filled with a catalyst containing Cu 3.7% w/w, K 1.4% w/w, 20% of the volume filled with a catalyst containing Cu 6% w/w, K 1% w/w and the last 20% filled with a catalyst containing Cu 7% w/w, K 1% w/w. The third reactor had only one type of catalyst containing Cu 7% w/w, K 1% w/w.

The first reactor was fed a mixture of 212 moles/h of ethylene, 85.7 moles/h of HCl, 17.5 moles/h of oxygen and 31 moles/h of nitrogen. The second reactor was fed 85.7 moles/h of HCl and 17.5 moles of oxygen. The third reactor was fed 8.75 moles/h of oxygen. At the inlet of the first reactor the oxygen concentration was 5% (−18% with respect to stoichiometric); at the inlet of the second reactor, the oxygen concentration was 4.6% (−30% with respect to stoichiometric); at the inlet of the third reactor the oxygen concentration was 3% (+9.6% with respect to stoichiometric). The overall oxygen excess was 2.1%. The inlet pressure of the first reactor was 6.3 bar and the outlet pressure at the third reactor was 4.25 bar. The temperature of the cooling jacket was held at 210° C.

The outlet stream, consisting of a mixture of ethylene, oxygen, HCl, EDC, water, COx and byproducts, was analyzed and the overall results were:

| | |
|---|---|
| Oxygen conversion to crude EDC | 97.70% |
| HCl conversion to crude EDC | 99.70% |
| EDC production | 85.55 moles/h |
| Hotspot 1° | 272 C° |
| 2° | 264 C° |
| 3° | 255 C° |
| Pressure drop° | 2.05 bar |

COMPARATIVE EXAMPLE 2

This example was carried out with only two reactors and with a catalytic loading scheme as in reactors 1 and 2 of Example 1. A mixture of ethylene (212 moles/h), (HCl 85.7 moles/h), oxygen (20.5 moles/h) and 31 moles of nitrogen was fed to the first stage. In the second stage, 85.7 moles/h of HCl and 23.25 moles/h of oxygen were fed. The oxygen concentration at the inlet of the first reactor was 5.9% (−4.5% with respect to stoichiometric); at the inlet of the second reactor the oxygen concentration was 6.05% (+4.22% with respect to stoichiometric). The results were:

| | |
|---|---|
| Oxygen conversion to crude EDC | 96.00% |
| HCl conversion to crude EDC | 98.20% |
| EDC production | 84.15 moles/h |
| Hotspot 1° | 316° C. |
| 2° | 313° C. |
| Pressure drop | 1.2 bar |

As we can see the hotspot temperature was too high.

COMPARATIVE EXAMPLE 3

The reaction was carried out with the same conditions as Example 2 but with a loading pattern arranged to lower the hotspot up to 270° C. In this case the catalyst activity was profiled to increase from top to the bottom, in the direction of reagent flow. The loading pattern was:

First reactor: 7% graphite; 48% of a catalyst containing Cu 2.7w/w, K 0.8% w/w, Cs 1% w/w; 23% of a catalyst containing Cu 3.3w/w K 1.1% w/w; and 22% of a catalyst containing Cu 7.8% w/w, K 0.8% w/w.

Second reactor: 7% graphite; 42% of a catalyst containing Cu 2.7% w/w, K 0.9% w/w; 30% of a catalyst containing Cu 5.5% w/w, K 0.6% w/w; and 21% of a catalyst containing Cu 7.8% w/w, K 0.8% w/w.

The oxygen concentration at the inlet of the reactors was the same as in Example 2. The results were:

| | |
|---|---|
| EDC production | 82.50 moles/h |
| HCl conversion | 96.23% |
| Oxygen conversion | 94.08% |
| Hotspots 1° | 275° C. |
| 2° | 275° C. |
| Pressure drop | 1.25 bar |

In this case the hot spot temperature was acceptable but the conversions of the oxygen and HCl were too low.

EXAMPLE 4

This Example was carried out with the same reactors and the same amount of reagents as in Example 2 but with the following catalytic scheme:

First reactor: The loading pattern was: 7% graphite; 3% of a catalyst containing Cu 6.5% w/w, K 2.2% w/w; 40% of a catalyst containing Cu 2.7% w/w, K 0.8% w/w; 22% of a catalyst containing Cu 3.75% w/w, K 1. 2% w/w; and 28% w/w of a catalyst containing Cu 7.8% w/w, K 0.8% w/w.

Second reactor: The loading pattern was: 3% of a catalyst containing Cu 6.5% w/w, K 2.2% w/w; 31% of a catalyst containing Cu 2.9% w/w, K 1.2% w/w; 18% of a catalyst containing Cu 3.9% w/w, K 1.3% w/w; and 48% of a catalyst containing Cu 7.8% w/w, K 0.8% w/w. The results were:

| | |
|---|---|
| Oxygen conversion to crude EDC | 96.80% |
| HCl conversion to crude EDC | 99.00% |
| EDC production | 85.00 moles/h |
| Hotspots 1° after 2.1 m | 270° C. |
| 2° after 2.1 m | 272° C. |
| Pressure drop | 1.25 bar |

Conversion and hotspots were good.

EXAMPLE 5

This example was carried out with the same apparatus and throughput in Example 3 but with the following loading scheme.

First reactor: 7% graphite, 3% of a catalyst containing Cu 6.5% w/w, K 2.2% w/w; 45% of a catalyst containing Cu 2.7% w/w, K 0.8% w/w; 28% of a catalyst containing Cu 3.75% w/w, K 1.2% w/w; and 22% of a catalyst containing Cu 7.8% w/w, K 0.8% w/w.

Second reactor: 3% of a catalyst containing Cu 6.5% w/w, K 2.2% w/w; 31% of a catalyst containing Cu 2.9% w/w, K 1.2% w/w; 20% of a catalyst containing Cu 3.9% w/w, K 1.3% w/w and 46% of a catalyst containing Cu 7.8% w/w.

The results were:

| | |
|---|---|
| Oxygen conversion to crude EDC | 96.50% |
| HCl conversion to crude EDC | 98.70% |
| EDC production | 84.75 moles/h |
| Hotspot 1° | 270° C. |
| 2° | 268° C. |
| Pressure drop | 1.25 bar |

Conversions and hotspots were good. Note the lowering of the pressure drop using the two stage system.

We claim:

1. A method for the oxychlorination of ethylene to produce 1,2-dichloroethane (EDC), comprising reacting ethylene, a chlorine source and an oxygen source in a fixed-bed oxychlorination reactor in the presence of a catalyst, characterised in that a twin reactor system is used and the catalyst is a cupric chloride catalyst whose activity profile is arranged such that the reagent flow first comes into contact with a first layer of high activity catalyst, subsequently a second layer of low activity catalyst and finally a third layer of high activity catalyst.

2. A method according to claim 1 wherein the third catalyst layer is a profiled catalyst comprising multiple catalyst layers wherein the activity increases in the direction of reagent flow.

3. A method according to claim 1 or claim 2 wherein the activity of the catalyst is profiled in each of the two reactors.

4. A method according to claim 3 wherein the temperature of the reaction does not exceed 285° C.

5. A method according to claim 3 wherein the catalyst also comprises promoters such as the chlorides of potassium, magnesium, cesium, lithium, sodium, calcium and cerium.

6. A method according to claim 3 wherein between 40 and 60% of the total oxygen source fed to the reaction is fed to the first reactor.

7. A method according to claim 3 wherein between 40 and 100% of the total chlorine source fed to the reaction is fed to the first reactor.

8. A method according to claim 3 wherein exhaust gases vented from the second reactor are recycled, at least in part, to the first reactor.

9. A method according to claim 3 wherein the reaction proceeds at a pressure between 4 and 7 barg.

* * * * *